United States Patent [19]

Waterhouse et al.

[11] Patent Number: 4,985,427
[45] Date of Patent: Jan. 15, 1991

[54] TRIAZINE DERIVATIVES

[75] Inventors: Ian Waterhouse; Alan Naylor; Christopher J. Wallis, all of Royston; Frank Ellis, Luton, all of England

[73] Assignee: Glaxo Group Limited, England

[21] Appl. No.: 344,667

[22] Filed: Apr. 28, 1989

[30] Foreign Application Priority Data

Apr. 29, 1988 [GB] United Kingdom ............... 8810185

[51] Int. Cl.$^5$ ............... C07D 253/075; A61K 31/53
[52] U.S. Cl. ................................. 514/242; 544/182
[58] Field of Search .................... 544/182; 514/242

[56] References Cited

FOREIGN PATENT DOCUMENTS 058534  8/1982  European Pat. Off.
154885  9/1985  European Pat. Off.
215354  3/1987  European Pat. Off.
299449  1/1989  European Pat. Off.

OTHER PUBLICATIONS

Busch, *Chem. Ber.*, 1903, 36, 3877-3890.
Heberlein, *Annalen*, 1898, 301, 58-69.

*Primary Examiner*—John M. Ford
*Attorney, Agent, or Firm*—Bacon & Thomas

[57] ABSTRACT

Compounds of formula (I)

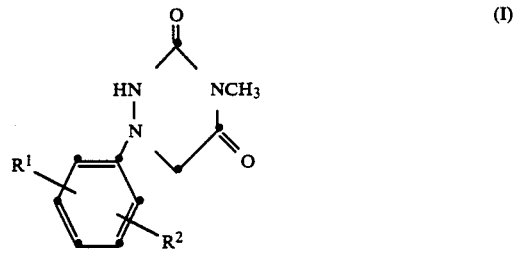

wherein $R^1$ is selected from the group consisting of hydrogen, halogen, hydroxy, $C_{1-6}$ alkyl, $C_{1-6}$ alkoxy, phenyl$C_{1-3}$alkoxy (in which the phenyl group is optionally substituted by a substituent selected from halogen, $C_{1-3}$ alkyl, $C_{1-3}$ alkoxy and hydroxy), nitro, trifluoromethyl, cyano, —$CO_2R^3$ (wherein $R^3$ is selected from hydrogen and $C_{1-4}$ alkyl) and —$CONR^4R^5$ (wherein $R^4$ and $R^5$ are each independently selected from hydrogen and $C_{1-4}$ alkyl, or $R^4$ and $R^5$ together with the nitrogen atom to which they are attached form a saturated 5- to 7- membered ring, which ring optionally contains one or more groups or atoms selected from oxygen, sulphur, —NH— and —N($CH_3$)—); and $R^2$ is selected from the group consisting of hydrogen, halogen, hydroxy, $C_{1-6}$ alkyl and $C_{1-6}$ alkoxy; and salts thereof are inhibitors of the enzyme 5-lipoxygenase.

Processes for preparing the compounds of formula (I) and compositions containing them are also described.

11 Claims, No Drawings

TRIAZINE DERIVATIVES

This invention relates to heterocyclic compounds, to processes for their preparation, to pharmaceutical compositions containing them and to their use in medicine. In particular, the invention relates to compounds which act as inhibitors of the enzyme 5-lipoxygenase.

The enzyme 5-lipoxygenase catalyses the first reaction in the biosynthesis of potent biological mediators, for example the leukotrienes (LTB$_4$, LTC$_4$, LTD$_4$, LTE$_4$), from arachidonic acid. The leukotrienes LTC$_4$, LTD$_4$ and LTE$_4$ and other 5-lipoxygenase products are widely believed to be the prime mediators in the pathogenesis of allergic asthma. The leukotriene LTB$_4$ is believed to be a mediator in the pathogenesis of inflammation. Thus compounds which inhibit the enzyme 5-lipoxygenase should reduce the production of these potent biological mediators and hence be useful for the treatment of diseases arising from the over-production of these mediators. Such diseases include respiratory diseases of the airways such as asthma, bronchitis, allergic rhinitis and sarcoidosis of the lung; inflammation of the gastrointestinal tract including gastritis, oesophagitis, duodenitis, inflammatory bowel disease (such as ulcerative colitis), irritable bowel syndrome, peptic ulceration, Crohn's disease and coeliac disease; inflammation of the joints including rheumatoid arthritis, rheumatoid spondylitis, osteoarthritis and gouty arthritis; diseases of the skin including psoriasis, eczema, contact dermatitis and atopic dermatitis; ischaemia of major organs including, brain, liver and kidney; ischaemic heart disease including angina and myocardial infarction and cardiovascular disorders such as peripheral vascular disease and cerebrovascular disease. In addition, compounds which inhibit the enzyme 5-lipoxygenase may be useful for suppressing tissue rejection following transplant surgery, and as cytoprotective agents.

Arachidonic acid is also an essential element in the biosynthesis of a number of other important mediators in the human body. It is therefore desirable that any 5-lipoxygenase inhibitor should have little or no effect on the biosynthesis of other mediators from arachidonic acid.

We have now found a novel group of triazine derivatives which are potent and selective inhibitors of the enzyme 5-lipoxygenase.

The synthesis of the following triazine derivative of formula (a):

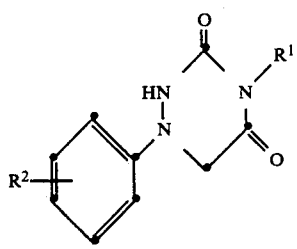

wherein R$^1$ and R$^2$ each represent a hydrogen atom was first described by G. Frerichs and H. Beckurts in Arch. Pharm., 1899, 237, 346–358. An alternative synthesis of this compound is described in Org. Khim., 1976, 99–102, which reference also describes the preparation of the compound of formula (a) wherein R$^1$ represents a hydrogen atom and R$^2$ represents a p-nitro group. The synthesis of the compound of formula (a) wherein R$^1$ represents an ethyl group and R$^2$ represents a hydrogen atom is described by M. Busch in Chem. Ber., 1903, 36, 3877–3890. However, no biological properties have been attributed to any of these three compounds.

The present invention provides triazine derivatives of the general formula (I):

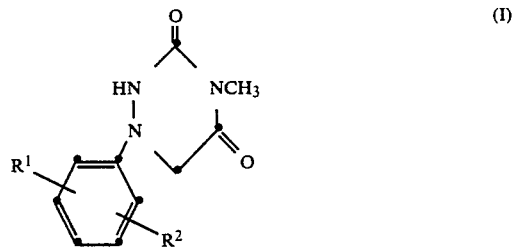

and salts thereof, in particular physiologically acceptable salts thereof, wherein R$^1$ represents a hydrogen or a halogen atom, or a group selected from hydroxy, C$_{1-6}$alkyl, C$_{1-6}$alkoxy, phenylC$_{1-3}$alkoxy (in which the phenyl group is unsubstituted or substituted by a halogen atom or a C$_{1-3}$alkyl, C$_{1-3}$alkoxy or hydroxy group), nitro, trifluoromethyl, cyano, —CO$_2$R$^3$ (wherein R$^3$ represents a hydrogen atom or a C$_{1-4}$alkyl group) and —CONR$^4$R$^5$ (wherein R$^4$ and R$^5$ each independently represents a hydrogen atom or a C$_{1-4}$alkyl group, or together with the nitrogen atom to which they are attached form a saturated 5- to 7-membered ring, which ring optionally contains one or more atoms selected from an oxygen or a sulphur atom, or a group —NH— or —N(CH$_3$)—); and R$^2$ represents a hydrogen or halogen atom, or a hydroxy, C$_{1-6}$alkyl or C$_{1-6}$alkoxy group.

Referring to the general formula (I), a halogen atom may be, for example, a fluorine, chlorine, bromine or iodine atom. An alkyl group (as such or as part of a group) may be a straight or branched chain alkyl group. A C$_{1-6}$alkyl group may be, for example, a methyl or a propyl group; a C$_{1-6}$alkoxy group may be, for example, a methoxy group; and a phenylC$_{1-3}$alkoxy group may be, for example, a benzyloxy group. The substituent(s) on the phenyl ring may be at the 2-, 3-, 4-, 5- or 6-position(s). Particular examples of a disubstituted phenyl group include phenyl substituted by two alkyl (e.g. methyl) groups or two halogen (e.g. fluorine) atoms.

According to one aspect, the invention provides compounds of formula (I) wherein R$^1$ represents a halogen atom, or a group selected from hydroxy, C$_{1-6}$alkyl, C$_{1-6}$alkoxy, phenylC$_{1-3}$alkoxy (in which the phenyl group is unsubstituted or substituted by a halogen atom or a C$_{1-3}$alkyl, C$_{1-3}$alkoxy or hydroxy group), nitro, trifluoromethyl, cyano, —CO$_2$R$^3$ and —CONR$^4$R$^5$ (R$^3$, R$^4$ and R$^5$ being as defined in formula (I)), and R$^2$ being as defined in formula (I).

A preferred class of compound of formula (I) is that in which R$^1$ represents a hydrogen or a halogen atom, or a group selected from hydroxy, C$_{1-6}$alkyl, C$_{1-6}$alkoxy, phenylC$_{1-3}$alkoxy, trifluoromethyl or cyano, and R$^2$ represents a hydrogen or a halogen atom, or a C$_{1-6}$alkyl group.

A particularly preferred class of compounds of formula (I) is that in which R$^1$ represents a hydrogen or a halogen (e.g. fluorine or chlorine) atom, or a phenylC- 1-3alkoxy (e.g. benzyloxy) group, and $R^2$ represents a hydrogen atom.

A further particularly preferred class of compounds, of formula (I) is that in which $R^1$ represents a fluorine atom, and $R^2$ represents a hydrogen atom.

A particularly preferred compound according to the invention is dihydro-1-(3-fluorophenyl)-4-methyl-1,2,4(triazine-3,5- (2H,4H)-dione and its physiologically acceptable salts.

Further preferred compounds according to the invention are dihydro-1-(4-fluorophenyl)-4-methyl-1,2,4-triazine-3,5-(2H,4H)-dione and dihydro-4-methyl-1-phenyl-1,2,4-triazine-3,5-(2H,4H)-dione, and their physiologically acceptable salts.

Suitable physiologically acceptable salts of the compounds of formula (I) include acid addition salts formed with organic or inorganic acids, for example hydrochlorides, hydrobromides, sulphates, methanesulphonates, phosphates, citrates, fumarates and maleates. The compounds of formula (I) may also form salts with suitable bases. Examples of such salts are alkali metal (e.g. sodium and potassium) salts.

All optical isomers of compounds of formula (I) and their mixtures including racemic mixtures thereof are embraced by the invention.

The selective 5-lipoxygenase inhibitory action of the compounds of the invention is readily demonstrated using human white blood cells. Thus in tests with human white blood cells stimulated with the compound A 23187, the compounds of the invention inhibit the synthesis of the leukotrienes $LTC_4$ and $LTD_4$ at concentrations which have little or no effect on the biosynthesis of other mediators from arachidonic acid.

Compounds of formula (I) are thus useful for the treatment of disease states in which the leukotrienes ($LTB_4$, $LTC_4$, $LTD_4$ and $LTE_4$) or other 5-lipoxygenase products are mediators.

Accordingly the invention provides a method of treatment for the relief or prevention of diseases in which leukotrienes or other 5-lipoxygenase products are mediators, which comprises administering to a human or animal subject an effective amount of a compound of formula (I) or a physiologically acceptable salt thereof.

It will be appreciated that compounds of the invention will primarily be of use in the alleviation of established symptoms, but prophylaxis is not excluded.

According to another aspect, the invention provides a pharmaceutical composition which comprises a compound of formula (I) or a physiologically acceptable salt thereof, formulated for administration by any convenient route, for use in human or veterinary medicine. Such compositions may be formulated in conventional manner using one or more physiologically acceptable carriers and/or excipients.

Thus the compounds of formula (I) may be formulated for oral, buccal, parenteral, topical or rectal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

For topical administration the pharmaceutical composition may take the form of ointments, lotions or creams formulated in a conventional manner, with for example an aqueous or oily base, generally with the addition of suitable thickening agents and/or solvents. For nasal applications, the composition may take the form of a spray, formulated for example as an aqueous solution or suspension or as an aerosol with the use of a suitable propellant.

The compounds of formula (I) may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in a powder form for constitution with a suitable vehicle, e.g. sterile pyrogen-free water, before use.

The compounds of formula (I) may also be formulated in rectal compositions such as suppositories or retention enemas, e.g. containing conventional suppository bases such as cocoa butter or other glycerides.

In addition to the formulations described previously, the compound may also be formulated as a depot preparation. Such long acting formulations may be administered by implantation (for example subcutaneously, transcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds for use according to the present invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of formula (I) and a suitable powder base such as lactose or starch.

The compositions may, if desired, be presented in a pack or dispenser device which may contain one or more unit dosage forms containing the active ingredient. The pack may for example comprise a metal or plastic foil, such as a blister pack. The pack or dispenser device may be accompanied by instructions for administration.

A proposed daily dose of the compound of the invention for administration to man (of approximately 70 kg body weight) is 1 mg to 2 g, which may be administered, for example, 1 to 4 times per day.

The precise dose will depend on the condition being treated, the route of administration, and the age and the body weight of the patient being treated.

Thus, for example, a suitable daily dose for oral administration is 100 mg to 2 g. For administration by inhalation or insufflation, a preferred dosage unit is 1 to 100 mg, more preferably 1 to 50 mg, which may be given 1 to 4 times daily.

In yet a further aspect the invention also provides for the use of a compound of formula (I) or a physiologically acceptable salt thereof for the manufacture of a medicament for the relief or prevention of diseases in which leukotrienes or other 5-lipoxygenase products are mediators.

The compounds of formula (I) and physiologically acceptable salts thereof may be prepared by the general methods outlined hereinafter. In the following description, the groups $R^1$ and $R^2$ are as defined for compounds of formula (I).

According to a first general process (A), a compound of formula (I) may be prepared by cyclising a compound of formula (II):

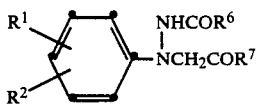
(II)

wherein $R^6$ represents the group $-OR^8$, where $R^8$ represents a lower alkyl (e.g. methyl) group and $R^7$ represents the group $-NHMe$, or $R^6$ represents the group $-NHMe$ and $R^7$ represents a leaving group such as $-OR^8$ (where $R^8$ is as defined previously), acyloxy (e.g. acetoxy), alkoxycarbonyloxy (e.g. methoxycarbonyloxy) or an imidazolide group.

In a particularly preferred embodiment of process (A), a compound of formula (I) may be prepared by cyclising a compound of formula (III):

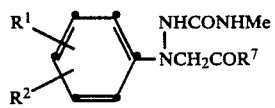
(III)

wherein $R^7$ represents a leaving group as defined above, preferably methoxy.

The cyclisation may be effected preferably using a base such as an alkali metal alkoxide (e.g. sodium methoxide or potassium t-butoxide) or an alkali metal hydroxide (e.g. sodium hydroxide), in a solvent such as an alcohol (e.g. methanol) or a ketone (e.g. methyl isobutyl ketone) conveniently at room temperature. Alternatively, the cyclisation may be carried out using an alkali metal hydride (e.g. sodium hydride) in an inert solvent such as tetrahydrofuran, conveniently at room temperature.

According to a particular aspect of this embodiment of general process (A), a compound of formula (I) may be prepared directly by the reaction of a compound of formula (IV):

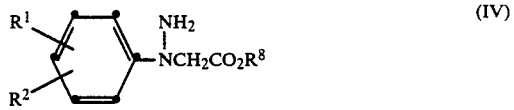
(IV)

wherein $R^8$ is as defined previously, with methyl isocyanate in a solvent such as acetonitrile and at an elevated temperature, followed by cyclisation as described above. In this particular embodiment, compounds of formula (III) may be isolated as intermediates.

Compounds of formulae (III) and (IV) are novel compounds and constitute a further aspect of this invention.

In a further embodiment of the cyclisation process (A), a compound of formula (I) may be prepared by cyclising a compound of formula (V):

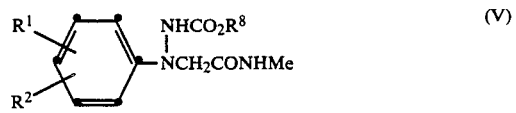
(V)

wherein $R^8$ represents a lower alkyl (e.g. methyl) group.

The cyclisation may be effected using a base such as an alkali metal alkoxide (e.g. sodium methoxide) in a solvent such as an alcohol (e.g. methanol or ethanol) and at a temperature in the range of 20° to 80° C. Alternatively, the cyclisation may be effected using a tetraalkylammonium fluoride (e.g. tetrabutylammonium fluoride) in a suitable solvent such as an ether (e.g. tetrahydrofuran) at room temperature or at an elevated temperature.

According to a particular aspect of this embodiment, a compound of formula (I) may be prepared directly by the reaction of a compound of formula (VI):

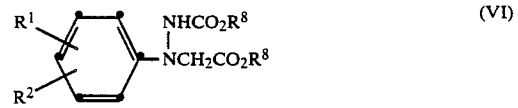
(VI)

wherein $R^8$ represents a lower alkyl (e.g. methyl) group, with methylamine and a base such as an alkali metal alkoxide (e.g. sodium methoxide) in a solvent such as an alcohol (e.g. methanol or ethanol) and at a temperature in the range 20° to 80° C. Compounds of formula (V) may be isolated as intermediates in this particular aspect of the embodiment.

Compounds of formula (III) in which $R^7$ represents the group $-OR^8$ may be prepared, for example, by the reaction of a compound of formula (IV), with methyl isocyanate. The reaction may conveniently be effected in a solvent such as acetonitrile and at an elevated temperature.

Compounds of formula (III) in which $R^7$ represents the group $-OR^8$ may also be prepared, for example, by reaction of a compound of formula (VII):

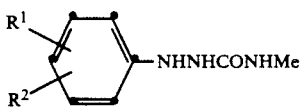

(VII)

with a compound of formula (VIII):

LCH₂CO₂R⁸   (VIII)

wherein L represents a leaving atom or group, preferably a halogen atom (e.g. a chlorine or a bromine atom), and $R^8$ is as defined previously, in the presence of a base such as an alkali metal hydrogen carbonate (e.g. sodium bicarbonate) or a tertiary amine (e.g. diisopropylethylamine) in a suitable solvent such as acetonitrile, an aromatic hydrocarbon (e.g. toluene), a substituted amide (e.g. dimethylformamide) or a ketone (e.g. methyl isobutyl ketone) and at an elevated temperature.

Compounds of formula (III) in which $R^7$ represents an acyloxy, alkoxycarbonyloxy or an imidazolide group may be prepared, for example, by reacting a compound of formula (IX):

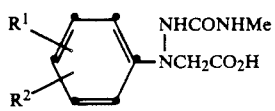

(IX)

or a salt thereof, with an appropriate acyl halide, alkyl chloroformate or imidazole derivative (e.g. N,N'-carbonyldiimidazole) respectively, using conventional techniques.

Compounds of formula (IV) may be prepared, for example, by the reaction of a compound of formula (X):

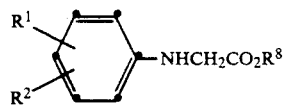

(X)

wherein $R^8$ is as defined previously, or a protected derivative thereof, with an appropriate nitrosating agent (e.g. an aqueous solution of sodium nitrite in acetic acid) at 0° C., followed by reduction using a suitable reducing agent (e.g. zinc dust).

Compounds of formula (VII) are either known or may be prepared, for example, by the reaction of a compound of formula (XI):

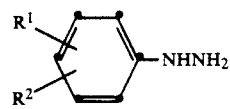

(XI)

with methyl urea. The reaction may conveniently be effected in a solvent such as water, and at the reflux temperature of the solvent.

Compounds of formula (IX) may be prepared by hydrolysis of a compound of formula (III) in which $R^7$ represents the group —$OR^8$ using conventional techniques.

Compounds of formula (X) are either known or may be prepared, for example, by the reaction of a compound of formula (XII):

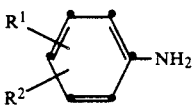

(XII)

with a compound of formula (VIII) in the presence of a base such as an alkali metal hydrogen carbonate (e.g. sodium bicarbonate) or sodium acetate trihydrate, optionally in a suitable solvent such as acetonitrile or an alcohol (e.g. methanol) and at an elevated temperature (conveniently the reflux temperature of the solvent).

Compounds of formula (V) may be prepared, for example, by the reaction of a compound of formula (VI) with methylamine. The reaction may conveniently be effected in an alcohol (e.g. methanol or ethanol) at 20° to 100° C.

Compounds of formula (VI) may be prepared, for example, by the reaction of a compound of formula (IV) with an alkyl chloroformate of formula $R^8OCOCl$ (in which $R^8$ is as defined previously) in a solvent such as a haloalkane (e.g. dichloromethane) and in the presence of an acid acceptor (e.g. pyridine).

The compounds of formulae (VIII), (XI) and (XII) are either known or may be prepared from known compounds by conventional procedures.

According to another general process (B), a compound of general formula (I) may be converted into another compound of formula (I) using conventional techniques.

Thus, according to one embodiment of the interconversion process, a compound of formula (I) in which $R^1$ represents a hydroxy group may be prepared, for example, by hydrogenation of the corresponding compound of formula (I) in which $R^1$ represents a benzyloxy group.

Hydrogenation may conveniently be effected in the presence of a catalyst such as platinum or palladium on a charcoal support, in a solvent such as an alcohol (e.g. ethanol or methanol), at normal or elevated temperature and pressure, for example from 20° to 100° C. and from 1 to 10 atmospheres.

A physiologically acceptable salt of a compound of formula (I) may be prepared by reacting a compound of formula (I) in the form of the free base with an appropriate acid or base using conventional methods.

Physiologically acceptable salts may also be prepared from other salts, including other physiologically acceptable salts, of a compound of formula (I) using conventional methods.

The various general methods described above may be used for the introduction of the desired groups at any stage in the stepwise formation of the required compound, and it will be appreciated that these general methods can be combined in different ways in such multi-step processes. The sequence of the reactions in multi-stage processes should of course be chosen so that the reaction conditions used do not affect groups in the molecule which are desired in the final product.

The invention is further illustrated by the following Preparations and Examples. All temperatures are in °C. Thin layer chromatography (t.l.c.) was carried out on silica, and flash column chromatography (FCC) was carried out on silica (Merck 9385). Petroleum ether refers to that fraction having b.p. 40°–60° C., unless otherwise stated. Organic extracts were dried over magnesium sulphate or sodium sulphate. Solvent System A denotes ether: petroleum ether and System B denotes ethyl acetate: petroleum ether. The following abbreviation is used: THF-tetrahydrofuran.

Intermediate 1

N-(3-Bromophenyl)glycine methyl ester

A mixture of 3-bromoaniline (88.6 g), methyl chloroacetate (44 ml), sodium acetate trihydrate (114 g) and methanol (70 ml) was heated under reflux for 18 h. The mixture was poured into water (500 ml) and extracted with dichloromethane (3×250 ml). The combined, dried organic extracts were evaporated and the residue was treated with 10% concentrated sulphuric acid in methanol (250 ml). After 3 h the solution was poured carefully into 8% sodium bicarbonate (1200 ml). The resulting solid was filtered off, dissolved in dichloromethane (1000 ml), and this solution was dried and evaporated to give a solid (94 g). A portion of this solid (1 g) was purified by FCC eluting with System A (1:1) to give a semi-solid which was recrystallised from System A to give the title compound, m.p. 66°–68°.

Intermediate 2

N-(3-Fluorophenyl)glycine methyl ester

3-Fluoroaniline (55.5 g), methyl chloroacetate (44 ml), and sodium acetate trihydrate (114 g) were treated according to the method of Intermediate 1 to give a solid (50 g), a small sample of which (ca. 1 g) was purified by FCC eluting with System B (1:3) to give a solid which was recrystallised from petroleum ether (60°–80°) to give the title compound, m.p. 68°–69°.

Intermediate 3

N-(3-Methoxyphenyl)glycine methyl ester

A mixture of 3-methoxyaniline (61.6 g), methyl chloroacetate (44 ml), sodium acetate trihydrate (114 g) and methanol (70 ml) was heated under reflux for 18 h. The mixture was poured into water (500 ml) and extracted with dichloromethane (3×250 ml). The combined, dried organic extracts were evaporated and the residue was treated with 10% concentrated sulphuric acid in methanol (250 ml). After 3 h the solution was poured carefully into 8% sodium bicarbonate (1200 ml) and partitioned with ether (4×500 ml). The combined organic extracts were washed successively with 0.5M citric acid solution (5×200 ml) and brine (500 ml), dried and evaporated to give an oil. Purification by FCC eluting initially with ether:petroleum ether 60°–80° (2:3) and then with ether:petroleum ether 60°–80° (1:1) gave the title compound (52 g) as an oil, t.l.c. (System A, 1:1) Rf 0.31.

Intermediate 4

N-[3-(Trifluoromethyl)phenyl]glycine methyl ester

3-Trifluoromethylaniline (80.5 g), methyl chloroacetate (44 ml) and sodium acetate trihydrate (114 g) were treated according to the method of Intermediate 1 to give a solid (84 g), a sample of which (ca. 1 g) was purified by FCC eluting with System A (1:1) to give a solid which was recrystallised from System A to give the title compound, m.p. 60°–63°.

Intermediate 5

N-(3-Methylphenyl)glycine methyl ester

A mixture of m-toluidine (55.0 g), methyl chloroacetate (85.0 g) and sodium bicarbonate (86.2 g) in acetonitrile (400 ml) was heated at reflux for 2 days under nitrogen. Ethyl acetate (250 ml) was added and the mixture was washed with water (2×250 ml), dried and evaporated to give an oil (120 g), a sample of which (1.4 g) was purified by FCC eluting with System A (3:7) to give the title compound (0.8 g) as a solid, m.p. 40°.

Intermediate 6

N-(3-Iodophenyl)glycine methyl ester

3-Iodoaniline (40.0 g), methyl chloroacetate (37.12 g) and sodium bicarbonate (30.75 g) were treated according to the method of Intermediate 5 to give an oil (ca. 80 g), a sample of which (1.2 g) was purified by FCC eluting with System A (7:3) to give the title compound (0.8 g) as a solid, m.p. 83°.

Intermediate 7

N-[3-(Phenylmethoxy)phenyl]glycine methyl ester

A suspension of 3-benzyloxyaniline (69.0 g) and sodium bicarbonate (58.1 g) in methyl chloroacetate (45.4 ml) was stirred at 80°–90° under nitrogen for 16 h. The resultant solid was poured into ether (400 ml) and the suspension was filtered. The collected solid was partitioned between water (400 ml) and dichloromethane (200 ml). The organic layer was separated and the aqueous layer was extracted with dichloromethane (2×200 ml). The combined organic extracts were dried and concentrated to give the title compound (66.9 g) as a solid, m.p. 92°–94°.

Intermediate 8

N-[4-(Trifluoromethyl)phenyl]glycine methyl ester

4-Trifluoromethylaniline (5.84 g), methyl chloroacetate (13.1 g) and sodium bicarbonate (3 g) were treated according to the method of Intermediate 5. The product was purified by FCC eluting with System B (1:3) to give the title compound (5.00 g), t.l.c. (System B, 1:3) Rf 0.32.

Intermediate 9

N-[4-(Phenylmethoxy)phenyl]glycine methyl ester

4-Benzyloxyaniline hydrochloride (70 g), methyl chloroacetate (49 ml) and sodium bicarbonate (75 g) in dry acetonitrile (200 ml) were heated at reflux for 6.5 h. Work up according to the method of Intermediate 7 gave a solid which was recrystallised from chloroform-hexane to give the title compound (55 g), m.p. 106°–107°.

Intermediate 10

N-(3,4-Dimethylphenyl)glycine methyl ester 3,4-Dimethylaniline (70.0 g) and methyl bromoacetate (44.2 g) were stirred at 100° under nitrogen for 2 h. The cooled reaction mixture was poured into ether (700 ml) and filtered. The collected solid was washed with ether (2×100 ml) and the combined filtrates were concentrated to give a solid (45.6 g) which was purified by FCC on triethylamine deactivated silica eluting with dichloromethane:petroleum ether (1:3) to give a solid (21.8 g), a portion of which (2.5 g) was purified further by FCC as above to give the title compound (2.06 g), m.p. 53°–55°.

Intermediate 11

N-(3,4-Difluorophenyl)glycine methyl ester

A suspension of 3,5-difluoroaniline (15.0 g) and sodium bicarbonate (19.5 g) in methyl chloroacetate (15.2 ml) was stirred at 80°–90° under nitrogen for 16 h. The cooled reaction mixture was poured into ether (100 ml) and filtered. The filtrate was washed with 2N aqueous hydrochloric acid (100 ml), dried and concentrated to give a solid (16.5 g) which was recrystallised from dichloromethane (20 ml) and n-hexane (40 ml) to give the title compound (9.21 g), m.p. 71°–73°.

Intermediate 12

N-(3,5-Difluorophenyl)glycine methyl ester

A suspension of 3,5-difluoroaniline (15.0 g) and sodium bicarbonate (19.5 g) in methyl chloroacetate (15.2 ml) was stirred at 80°–90° under nitrogen for 60 h. More sodium bicarbonate (4.88 g) and methyl chloroacetate (5.1 ml) were added, and the suspension was stirred at 80°–90° for a further 24 h. Work up according to the method of Intermediate 11 gave a solid (16 g) which was recrystallised from chloroform (10 ml) and n-hexane (120 ml) to give the title compound (8.34 g), m.p. 75°–77°.

The mother liquors from the recrystallisation were concentrated and triturated with n-hexane (100 ml) to give a further amount of the title compound (1.83 g).

Intermediate 13

N-(2,4-Difluorophenyl)glycine methyl ester

A suspension of 2,4-difluoroaniline (15.0 g) and sodium bicarbonate (19.5 g) in methyl chloroacetate (15.2 ml) was stirred at 90°–100° under nitrogen for 16 h. Work up according to the method of Intermediate 11 gave an oil (14.1 g) which was purified by FCC on triethylamine deactivated silica eluting with chloroform:petroleum ether (1:8) to give the title compound (8.75 g) as an oil, t.l.c. on triethylamine deactivated silica (chloroform:petroleum ether, 1:8) Rf 0.21.

Intermediate 14

N-(2,6-Difluorophenyl)glycine methyl ester

A suspension of 2,6-difluoroaniline (15.0 g) and sodium bicarbonate (19.5 g) in methyl chloroacetate (15.2 ml) was stirred at 90°–100° under nitrogen for 16 h. Methyl bromoacetate (11.0 ml) and sodium bicarbonate (9.75 g) were added, and the suspension was stirred at 90°–100° for a further 5 h. Work up according to the method of Intermediate 11 gave an oil (14.7 g) which was purified by FCC eluting with system A (1:8) to give the title compound (8.27 g) as an oil, t.l.c. (System A, 1:8) Rf 0.3.

Intermediate 15

Methyl [1-(3-bromophenyl)hydrazino]acetate

A solution of sodium nitrite (30 g) in water (200 ml) was added dropwise to a solution of N-(3-bromophenyl)glycine methyl ester (94 g) in aqueous acetic acid (850 ml) at 0°. After 1 h, methanol (200 ml) was added and the mixture was cooled to −10°. Zinc dust (351 g) was added portionwise over 2 h during which time the temperature was maintained at −10° to 0°. The mixture was then allowed to warm to room temperature, poured into ethyl acetate (1000 ml) and filtered. The filtrate was poured into water (1000 ml) and the layers were separated. The organic extract was washed with 2N sodium carbonate solution (500 ml) and solid sodium carbonate was added until the solution was basic. The aqueous extract was re-extracted using ethyl acetate (1000 ml) and the combined organic extracts were dried and evaporated. The residue was purified by FCC eluting with System A (1:1) to give the title compound (25.1 g) as an oil, t.l.c. (System A, 1:1) Rf 0.26.

Intermediate 16

Methyl [1-(3-fluorophenyl)hydrazino]acetate

N-(3-Fluorophenyl)glycine methyl ester (10.0 g) was treated according to the method of Intermediate 15, using zinc powder (14.3 g). The residue was purified by FCC eluting with ether:petroleum ether (60°–80°) (1:1) to give the title compound (4.56 g) as an oil, t.l.c. (ether:petroleum ether (60°–80°), 1:1) Rf 0.16.

Intermediate 17

Methyl [1-(3-methoxyphenyl)hydrazino]acetate

To a cold (0°) solution of N-(3-methoxyphenyl)glycine methyl ester (50 g) in aqueous acetic acid (800 ml) was added dropwise an aqueous solution (200 ml) of sodium nitrite (21.2 g) and the mixture was stirred for 30 min. Methanol (200 ml) was added and the mixture was cooled to −10°. Zinc dust (83.2 g) was added portionwise over 2 h during which time the internal temperature was maintained at −10° to 0° and the mixture was stirred for a further 1 h at 0°. Dichloromethane (800 ml) and water (800 ml) were added and the resulting suspension was filtered. The filtrate was diluted with more water (500 ml) and dichloromethane (500 ml). The phases were separated and the aqueous layer was partitioned with more dichloromethane (2×500 ml). The combined organic extracts were washed with water (3×500 ml) and evaporated in vacuo. The residual oil was treated with 8% sodium bicarbonate (1000 ml) and partitioned with ether (3×700 ml). The combined organic layers were washed with brine (500 ml), dried and evaporated. Purification by FCC eluting with System A (1:1) and then System A (7:3) gave the title compound (8.2 g) as an oil, t.l.c. (System A, 1:1) Rf 0.12.

Intermediates 18 to 33 and 39 to 41 were prepared in a similar manner to Intermediate 15, using only 3 to 5 equivalents of zinc dust, and in some cases the organic solution was basified with anhydrous sodium bicarbonate or with sodium bicarbonate solution instead of sodium carbonate. In addition, Intermediates 28, 31, 32, 33, 39 and 41 were prepared without the addition of methanol to the reaction mixture prior to adding the zinc dust.

Intermediate 18

Methyl [1-[3-(trifluoromethyl)phenyl]hydrazino]acetate

The title compound (22.2 g) was obtained as an oil, t.l.c. (System B, 1:3) Rf 0.28, from N-[3-(trifluoromethyl)phenyl]glycine methyl ester (84 g). The product was purified by FCC eluting with System B (1:3).

Intermediate 19

Methyl [1-(3-methylphenyl)hydrazino]acetate

The title compound (18.0 g) was obtained as an oil, t.l.c. (System B, 1:9) Rf 0.15, from N-(3-methylphenyl)glycine methyl ester (116 g). The product was purified by FCC eluting with System B (1:9).

Intermediate 20

Methyl [1-(3-iodophenyl)hydrazino]acetate

The title compound (20.1 g) was obtained as an oil from N-(3-iodophenyl)glycine methyl ester (61.0 g). The product was purified by FCC eluting with System B (1:4), and a portion (1.0 g) was then rechromatographed under the same conditions to give the title compound (0.7 g), t.l.c. (System B, 1:4) Rf 0.13.

Intermediate 21

Methyl [1-[3-(phenylmethoxy)phenyl]hydrazino]acetate

The title compound (4.56 g) was obtained as an oil, t.l.c. (System B, 1:5) Rf 0.36, from N-[3-(phenylmethoxy)phenyl]glycine methyl ester (22 g). The product was purified by FCC eluting with System B (1:5).

Intermediate 22

Methyl [1-(4-methoxyphenyl)hydrazino]acetate

The title compound (11.12 g) was obtained as an oil, t.l.c. (System A, 6:1) Rf 0.27, from N-(4-methoxyphenyl)glycine methyl ester (60.0 g). The product was purified by FCC eluting with System A (6:1).

Intermediate 23

Methyl [1-(4-methylphenyl)hydrazino]acetate

The title compound (12.0 g) was obtained as an oil, t.l.c. (ether) Rf 0.5, from N-(4-methylphenyl)glycine methyl ester (19.0 g). The product was isolated by extraction with dichloromethane (instead of ethyl acetate) and was purified by FCC eluting with System A (2:3).

Intermediate 24

Methyl [1-(4-fluorophenyl)hydrazino]acetate

The title compound (2.12 g) was obtained as an oil, t.l.c. (System B, 1:3) Rf 0.37, from N-(4-fluorophenyl)glycine methyl ester (15.0 g). The product was purified by FCC eluting with System B (1:3).

Intermediate 25

Methyl [1-[(4-trifluoromethyl)phenyl]hydrazino]acetate

The title compound (3.23 g) was obtained as an oil, t.l.c. (System B, 1:8) Rf 0.29, from N-[4-(trifluoromethyl)phenyl]glycine methyl ester (6.86 g). The product was purified by FCC eluting with System B (1:9).

Intermediate 26

Methyl [1-(2-methylphenyl)hydrazino]acetate

The title compound (3.1 g) was obtained as an oil, t.l.c. (System B, 1:8) Rf 0.3, from N-(2-methylphenyl)glycine methyl ester (18.7 g). The product was purified by FCC eluting with System B (1:8) and was then purified further by FCC eluting with System B (1:1).

Intermediate 27

Methyl [1-[4-(phenylmethoxy)phenyl]hydrazino]acetate

The title compound (6.02 g) was obtained as a solid, m.p. 72°–73°, from N-[4-(phenylmethoxy)phenyl]glycine methyl ester (50 g). The product was purified by FCC on triethylamine deactivated silica eluting with chloroform:petroleum ether (1:1).

Intermediate 28

Methyl [1-(2-fluorophenyl)hydrazino]acetate

The title compound (5.7 g) was obtained as an oil, t.l.c. (System B, 2:5), from N-(2-fluorophenyl)glycine methyl ester (25.1 g). The product was purified by FCC eluting with System B (2:5).

The products of Intermediates 29 to 33 were purified by FCC eluting with chloroform.

Intermediate 29

Methyl [1-(3,4-dimethylphenyl)hydrazino]acetate

The title compound (6.25 g) was obtained as an oil, t.l.c. (chloroform) Rf 0.17, from N-(3,4-dimethylphenyl)glycine methyl ester (19.23 g).

Intermediate 30

Methyl [1-(3,4-difluorophenyl)hydrazino]acetate

The title compound (4.60 g) was obtained as an oil, t.l.c. (chloroform) Rf 0.2, from N-(3,4-difluorophenyl)glycine methyl ester (9.56 g).

Intermediate 31

Methyl [1-(3,5-difluorophenyl)hydrazino]acetate

The title compound (2.98 g) was obtained as an oil, t.l.c. (chloroform) Rf 0.21, from N-(3,5-difluorophenyl)glycine methyl ester (8.00 g).

Intermediate 32

Methyl [1-(2,4-difluorophenyl)hydrazino]acetate

The title compound (2.63 g) was obtained as an oil, t.l.c. (chloroform) Rf 0.2, from N-(2,4-difluorophenyl)glycine methyl ester (8.60 g).

Intermediate 33

Methyl [1-(2,6-difluorophenyl)hydrazino]acetate

The title compound (1.85 g) was obtained as an oil, t.l.c. (chloroform) Rf 0.16, from N-(2,6-difluorophenyl)glycine methyl ester (8.18 g).

Intermediate 34

Methyl [1-(3-methoxyphenyl)-2-[(methylamino)carbonyl]hydrazino]acetate

A solution of methyl [1-(3-methoxyphenyl)hydrazino]acetate (1.6 g) and methyl isocyanate (0.9 ml) in acetonitrile (20 ml) was heated under reflux for 1 h. The solvent was removed in vacuo and the residue was treated with ether to give the title compound (1.8 g) as a solid, m.p. 145°–146°.

Intermediate 35

Methyl [1-(3-iodophenyl)-2-[(methylamino)carbonyl]hydrazino]acetate

Methyl isocyanate (1.24 g) was added to a solution of methyl [1-(3-iodophenyl)hydrazino]acetate (3.0 g) in acetonitrile (50 ml) and the mixture was stirred under nitrogen for 2 h. The mixture was added to pH 6.5 phosphate solution (150 ml) and extracted with ethyl acetate (200 ml). The organic phase was washed with brine (100 ml) and water (100 ml), dried and evaporated to give a solid (3.0 g) which was crystallised from ethyl acetate to give the title compound (2.0 g), m.p. 150°.

Intermediate 36

N-(3-Propylphenyl)glycine methyl ester

A mixture of 3-propylaniline (20 g), sodium bicarbonate (24.9 g) and methyl chloroacetate (24.0 g) were stirred under nitrogen at 80°–90° for 24 h. The cooled reaction mixture was poured into ether (100 ml) and filtered. The filtrate was washed with water (100 ml), dilute hydrochloric acid (100 ml) and water (100 ml), then dried and concentrated in vacuo. The oily product (21.2 g) was distilled to give the title compound as a liquid, b.p. 160° at 0.35 mmHg, which solidified to give a low melting solid (16.1 g).

Intermediate 37

N-(3-Chlorophenyl)glycine methyl ester

A mixture of sodium bicarbonate (66 g), 3-chloroaniline (50 g) and methyl chloroacetate (51.5 ml) were stirred under nitrogen at 80°–100° for 6 h. Heating at 90° was continued overnight, and the mixture was then cooled and poured into ether (400 ml). The resultant suspension was stirred, chilled to 0°, the precipitated solid was filtered off and the filtrate was retained. The solid was dissolved in ethyl acetate (400 ml) and washed with water (2×200 ml), followed by dilute hydrochloric acid (200 ml). The organic phase was dried and concentrated in vacuo to give the title compound (16.4 g) as a solid, m.p. 75°–76°. The previously obtained filtrate was washed with dilute hydrochloric acid (200 ml), and the organic phase was separated, dried and concentrated in vacuo to give an oily solid. This was triturated with ether:hexane (1:1; 300 ml) and filtered off to give a further batch of the title compound (20 g).

Intermediate 38

N-(3-Cyanophenyl)glycine methyl ester

A mixture of sodium bicarbonate (35.5 g), methyl chloroacetate (28 ml) and 3-aminobenzonitrile (25 g) were stirred under nitrogen at 80°–100° for 6 h. Heating at 90° was continued overnight, and the mixture was then cooled and poured into ether (400 ml). The solid precipitate was filtered off and the filtrate was retained. The solid was dissolved in dichloromethane (400 ml) and washed with water (200 ml) followed by dilute hydrochloric acid (200 ml). The organic phase was dried and concentrated in vacuo to give the title compound as a solid (13.8 g), m.p. 91.5°–92.5°. The previously obtained filtrate was washed with water (100 ml), dilute hydrochloric acid (200 ml) and water (100 ml), then dried and concentrated in vacuo. The resultant solid was triturated with ether to give a further batch of the title compound (11.7 g).

Intermediates 39 to 41 were prepared in a similar manner to Intermediate 15.

Intermediate 39

Methyl [1-(3-propylphenyl)hydrazino]acetate

The title compound (1.4 g) was obtained as an oil, t.l.c. (chloroform:ethanol, 98:2) Rf 0.17, from N-(3-propylphenyl)glycine methyl ester (10 g). The product was purified by FCC eluting with chloroform:ethanol (98:2).

Intermediate 40

Methyl [1-(3-chlorophenyl)hydrazino]acetate

The title compound (3.25 g) was obtained as an oil, t.l.c. (dichloromethane:ethyl acetate, 9:1) Rf 0.49, from N-(3-chlorophenyl)glycine methyl ester (10 g). The product was purified by FCC eluting with dichloromethane followed by dichloromethane:ethyl acetate (4:1).

Intermediate 41

Methyl [1-(3-cyanophenyl)hydrazino]acetate

The title compound (1.8 g) was obtained as a solid, m.p. 78°–79°, from N-(3-cyanophenyl)glycine methyl ester (5 g). The product was purified by FCC eluting with dichloromethane.

Intermediate 42

Methyl [2-[(methylamino)carbonyl]-1-(3-propylphenyl)hydrazino]acetate

Methyl [1-(3-propylphenyl)hydrazino]acetate (700 mg) was dissolved in acetonitrile (10 ml) under nitrogen at room temperature. Methyl isocyanate (0.69 ml) was added to the solution which was then heated at 80° for 85 min. The solvent was removed in vacuo and the residue was dissolved in ether (10 ml). Hexane (20 ml) was added to precipitate a solid which was filtered off to give the title compound (677 mg), m.p. 76°–77°.

Intermediate 43

Methyl [1-(3-chlorophenyl)-2-[(methylamino)carbonyl]hydrazino]acetate

Methyl [1-(3-chlorophenyl)hydrazino]acetate (1.78 g) was dissolved in acetonitrile (20 ml) under nitrogen at room temperature. Methyl isocyanate (1.7 ml) was added to the solution which was then heated at 80° for 2 h. The solvent was removed in vacuo to give an oily residue which solidified on standing. This solid was triturated with ether and filtered to give the title compound (2.0 g), m.p. 121°–122°.

Intermediate 44

Methyl [2-[(methylamino)carbonyl]-1-phenylhydrazino]acetate

A mixture of 4-methyl-1-phenylsemicarbazide (20.0 g), methyl bromoacetate (27.75 g) and diisopropylethylamine (23.2 ml) in toluene (200 ml) under nitrogen was heated at 90° to 100° for 25 h with stirring. Toluene (120 ml) was then distilled off at ca. 90° under reduced pressure. The mixture was cooled to <50° and diluted with water (120 ml) and ethyl acetate (200 ml). The organic phase was separated and washed with water (60 ml). The two aqueous phases were extracted sequentially with ethyl acetate (2×60 ml). The combined organic phases were filtered and concentrated to 80 ml at atmospheric pressure. Toluene (100 ml) was added and the solution was again concentrated to 80 ml. The concentrate was seeded at ca. 80° with an authentic sample of the title compound, and allowed to cool to ca. 20° overnight. The resultant solid was filtered off, washed with toluene (20 ml) followed by t-butyl methyl ether (20 ml), and dried in vacuo for 24 h to give the title compound (22.39 g), m.p. 122°–122.5°.

Intermediate 45

Methyl [[2-[(methoxycarbonyl)amino]-1-phenyl]hydrazino]acetate

To a cooled (−10°) solution of methyl chloroformate (0.62 ml) in dichloromethane (20 ml) was added dropwise over 0.5 h a solution of methyl (1-phenylhydrazino)acetate (1.32 g) and pyridine (1.2 ml) in dichloromethane (15 ml). After 0.5 h the mixture was diluted with dichloromethane (50 ml), washed with pH 6 phosphate buffer solution (50 ml) and water, then dried and evaporated to give the title compound (1.75 g) as a solid, m.p. 105°–109°.

Intermediate 46

2-[(Methoxycarbonyl)amino]-N-methyl-1-phenylhydrazineacetamide

Methylamine in ethanol (33% w/w; 2 ml) was added to a suspension of methyl [[2-[(methoxycarbonyl)amino]-1-phenyl]hydrazino]acetate (838 mg) in methanol (8 ml). After 17 h the solvent was removed in vacuo to give the title compound (840 mg) as a foam.

Analysis Found: C,55.9; H,6.6; N,16.8; $C_{11}H_{15}N_3O_3$ requires C,55.7; H,6.4; N,17.7%.

EXAMPLE 1

Dihydro-1-(3-bromophenyl)-4-methyl-1,2,4-triazine-3,5-(2$\underline{H}$,4$\underline{H}$)-dione A solution of methyl [1-(3-bromophenyl)hydrazino]acetate (2.5 g) and methyl isocyanate (1.46 ml) in acetonitrile (20 ml) was heated under reflux for 2 h. The solvent was removed in vacuo and methanol (20 ml) was added to the residue which was then treated with a solution of sodium methoxide in methanol (30 ml; from 556 mg of sodium). After 1 h at 20° the solution was neutralised with acetic and the solvent was removed in vacuo. The residue was taken into ethyl acetate (250 ml), washed with pH 6 phosphate buffer solution (250 ml), dried and evaporated. Crystallisation of the residue from System B gave the title compound (316 mg). The mother liquor was evaporated, and the resulting solid was triturated with ether to give a further quantity of the title compound (335 mg), m.p. 165°–166°, t.l.c. (ether) Rf 0.41.

EXAMPLE 2

Dihydro-1-(3-fluorophenyl)-4-methyl-1,2,4-triazine-3,5-(2$\underline{H}$,4$\underline{H}$)-dione Methyl [1-(3-flourophenyl)hydrazino[acetate (1.31 g) was treated with methyl isocyanate (1 ml) and then with sodium methoxide in methanol (20 ml; from sodium (380 mg)) according to the method of Example 1. The product was crystallised from ethyl acetate-light petroleum (60°–80°) to give the title compound (781 mg), m.p. 193°–196°.

Analysis Found: C,53.7; H,4.5; N,18.8; $C_{10}H_{10}FN_3O_2$ requires C,53.8; H,4.5; N,18.8%.

EXAMPLE 3

Dihydro-1-(3-methoxyphenyl)-4-methyl-1,2,4-triazine-3,5-(2$\underline{H}$,4$\underline{H}$)-dione To a solution of methyl [1-(3-methoxyphenyl)-2-[(methylamino)carbonyl]hydrazino]acetate (1.6 g) in methanol (20 ml) under nitrogen was added a solution of sodium methoxide (8 ml; from sodium (5.2 g) in methanol (150 ml)). After 1 h the mixture was poured into pH 6 phosphate buffer (100 ml) and partitioned with dichloromethane (3×50 ml). The combined, dried organic extracts were evaporated to give a solid which was purified by FCC eluting with System A (7:3) to give, after trituration with System A (1:1), the title compound (650 mg), m.p. 120°–122°.

Analysis Found: C,56.3; H,5.6; N,17.8; $C_{11}H_{13}N_3O_3$ requires C,56.2; H,5.6; N,17.9%.

EXAMPLE 4

Dihydro-4-methyl-1-[3-(trifluoromethyl)phenyl]-1,2,4-triazine-3,5-(2$\underline{H}$,4$\underline{H}$)-dione Methyl [1-[3-(trifluoromethyl)phenyl]hydrazino]acetate (5 g) was treated with methyl isocyanate (3.05 ml) and then with sodium methoxide in methanol (60 ml; from sodium (1.16 g)) according to the method of Example 1. The product was purified by FCC eluting with System A (19:1) to give a solid, which was crystallised from System B to give the title compound (1.3 g), m.p. 163°–165°.

Analysis Found: C,48.5; H,3.6; N,15.3; $C_{11}H_{10}F_3N_3O_2$ requires C,48.4; H,3.7; N,15.4%.

EXAMPLE 5

Dihydro-4-methyl-1-(3-methylphenyl)-1,2,4-triazine-3,5-(2$\underline{H}$,4$\underline{H}$)-dione Methyl isocyanate (2.65 g) was added to a solution of methyl [1-(3-methylphenyl)hydrazino]acetate (3.0 g) in acetonitrile and the mixture was stirred under nitrogen for 4 h. The mixture was added to pH 6.5 phosphate buffer solution (50 ml) and dichloromethane (100 ml) was added. The organic extract was washed with brine (150 ml), dried, and evaporated to give a solid (3.95 g) which was dissolved in methanol (80 ml), and sodium methoxide (from sodium (1.0 g) in methanol (55 ml)) was slowly added. The solution was stirred under nitrogen for 30 min, and the mixture was then added to pH 6.5 phosphate solution (150 ml) and extracted with dichloromethane (150 ml). The organic phase was washed with brine (100 ml) and water (100 ml), dried and evaporated to give a solid which was triturated with System B (1:1) to give the title compound (0.7 g), m.p. 173°–175°, t.l.c. (System B, 3:7), Rf 0.5.

EXAMPLE 6

Dihydro-1-(3-iodophenyl)-4-methyl-1,2,4-triazine-3,5-(2$\underline{H}$,4$\underline{H}$)-dione Methyl [1-(3-iodophenyl)-2-[(methylamino)carbonyl]hydrazino]acetate (2.0 g) was dissolved in methanol (60 ml) and sodium methoxide (0.64 g) was added. The solution was stirred under nitrogen for 1.5 h, added to pH 6.5 phosphate buffer solution (150 ml) and extracted with dichloromethane (100 ml). The organic phase was washed with water (100 ml) and brine (100 ml), dried and evaporated to give the title compound as a solid (0.6 g), m.p. 180°.

Analysis Found C,36.4; H,3.1; N,12.5; $C_{10}H_{10}IN_3O_2$ requires C,36.6; H,3.0; N,12.7%.

EXAMPLE 7

Dihydro-4-methyl-1-[3-(phenylmethoxy)phenyl[-1,2,4-triazine-3,5-(2$\underline{H}$,4$\underline{H}$)-dione A mixture of methyl [1-[3-(phenylmethoxy)phenyl]-hydrazino acetate (4.5 g) and methyl isocyanate (2.38 ml) in acetonitrile (30 ml) was heated under reflux for 2 h. The solvent was removed in vacuo and the residue was taken into methanol (30 ml) and treated with a solution of sodium methoxide (from sodium (812 mg) in methanol (45 ml)). After 1 h at 20° the solution was neutralised with acetic acid and the solvent was removed in vacuo. The residue was taken into ethyl acetate (100 ml) and washed with water (100 ml). The aqueous phase was then re-extracted using ethyl acetate (100 ml) and the combined organic extracts were washed with saturated brine (100 ml), dried and evaporated. The resultant solid was then taken into ethyl acetate and washed with water (100 ml). The organic phase was filtered and the filtrate was washed with saturated brine (100 ml), dried and evaporated. The resultant solid was purified by FCC eluting with System B (1:1) to give a solid (0.98 g) which was triturated with ether to give the title compound (0.95 g), m.p. 147°–148°.

Analysis Found: C,65.7; H,5.5; N,13.2; $C_{17}H_{17}N_3O_2$ requires C,65.6; H,5.5; N,13.5%.

EXAMPLE 8

Dihydro-1-(4-methoxyphenyl)-4-methyl-1,2,4-triazine-3,5-(2H,4H)-dione

Methyl [1-(4-methoxyphenyl)hydrazino]acetate (1.50 g) was treated with methyl isocyanate (0.85 ml) and then with sodium methoxide (from sodium (0.33 g) in methanol (15 ml)) according to the method of Example 1. The product was purified by recrystallisation from ethyl acetate to give the title compound (703 mg), m.p. 179°–181°, t.l.c. (ether) Rf 0.5.

EXAMPLE 9

Dihydro-4-methyl-1-(4-methylphenyl)-1,2,4-triazine-3,5-(2H,4H)-dione

To a solution of methyl [1-(4-methylphenyl)hydrazino]acetate (2.25 g) in acetonitrile (10 ml) was added methyl isocyanate (2 ml) and the mixture was heated under reflux for 30 min. The solvent was removed in vacuo to give a solid which was treated with a solution of sodium methoxide (27 ml; from sodium (4 g) and methanol (200 ml)) according to the method of Example 3 to give a solid which was purified by trituration with System A (1:1) to give the title compound (1.51 g), m.p. 193°–194°, t.l.c. (ether) Rf 0.56.

EXAMPLE 10

Dihydro-1-(4-fluorophenyl)-4-methyl-1,2,4-triazine-3,5-(2H,4H)-dione

A mixture of methyl [1-(4-fluorophenyl)hydrazino]acetate (2.12 g) and methyl isocyanate (1.63 ml) in acetonitrile (20 ml) was heated under reflux for 3 h. The solvent was removed in vacuo and the residual oil was taken into methanol (20 ml) and treated with a solution of sodium methoxide (from sodium (556 mg) in methanol (30 ml)). After 1 h at 20° the solution was neutralised with acetic acid and the solvent was removed in vacuo. The residue was taken into ethyl acetate (100 ml), washed with pH 6 phosphate buffer (100 ml), dried and evaporated. Crystallisation of the residue from System B gave the title compound (1.10 g), m.p. 205°–206°.

Analysis Found: C,53.7; H,4.4; N,18.9; $C_{10}H_{10}FN_3O_2$ requires C,53.8; H,4.5; N,18.8%.

EXAMPLE 11

Dihydro-4-methyl-1-[4-(trifluoromethyl)phenyl]-1,2,4-triazine-3,5-1,2,4-triazine-3,5(2H,4H)-dione Methyl [1-[(4-trifluoromethyl)phenyl]hydrazino]acetate (2.48 g) was treated with methyl isocyanate (2 ml) and then with a solution of sodium methoxide (23 ml; from sodium (4 g) and methanol (200 ml)) according to the method of Example 9 to give the title compound (1.24 g), m.p. 193°–194°, t.l.c. (ether) Rf 0.52.

EXAMPLE 12

Dihydro-4-methyl-1-(2-methylphenyl)-1,2,4-triazine-3,5-(2H,4H)-dione

Methyl [1-(2-methylphenyl)]hydrazino]acetate (2.0 g) was treated with methyl isocyanate (1.2 ml) and then with a solution of sodium methoxide (from sodium (0.52 g) in methanol (30 ml)) according to the method of Example 7 to give the title compound (0.60 g), m.p. 147°–148°.

Analysis Found: C,60.2; H,6.0; N,19.1; $C_{11}H_{13}N_3O_2$ requires: C,60.3; H,6.0; N,19.2%.

Examples 13 to 19 were prepared in a similar manner to Example 9, although in Examples 13 and 14, ethyl acetate was used instead of dichloromethane to extract the aqueous reaction mixture. In each case the solid product was triturated with ether before any subsequent purification. Sodium methoxide solution refers to a 1.85M solution in methanol, unless otherwise stated.

EXAMPLE 13

Dihydro-4-methyl-1-[4-(phenylmethoxy)phenyl]-1,2,4-triazine-3,5-(2H,4H)-dione

Methyl [1-[4-(phenylmethoxy)phenyl]hydrazino]acetate (0.73 g) was treated with methyl isocyanate (0.5 ml) and then with sodium methoxide solution (3.5 ml). The product was recrystallised from tetrahydrofuran-hexane to give the title compound (0.56 g), m.p. 224°–227°, t.l.c. (ethyl acetate) Rf 0.55.

EXAMPLE 14

Dihydro-1-(2-fluorophenyl)-4-methyl-1,2,4-triazine-3,5-(2H,4H)-dione

Methyl [1-(2-fluorophenyl)hydrazino]acetate (1.80 g) was treated with methyl isocyanate (1.1 ml) and then with sodium methoxide solution (9.81 ml) to give the title compound (1.1 g), m.p. 162°–163°.

Analysis Found: C,53.7; H,4.5; N,18.4; $C_{10}H_{10}FN_3O_2$ requires C,53.8; H,4.5; N,18.8%.

EXAMPLE 15

Dihydro-4-methyl-1-(3,4-dimethylphenyl)-1,2,4-triazine-3,5-(2H,4H)-dione

Methyl [1-(3,4-dimethylphenyl)hydrazino]acetate (3.0 g) was treated with methyl isocyanate (0.93 ml) and then with sodium methoxide (1.63M solution in methanol; 17.7 ml) to give a solid (2.19 g). A portion of this solid (1.0 g) was recrystallised from 2-propanol (40 ml), filtered off, washed with ice-cold 2-propanol (2×5 ml), and dried at 60°, 0.1 torr for 16 h to give the title compound (0.71 g), m.p. 200°–202°.

Analysis Found: C,61.6; H,6.7; N,18.2; $C_{12}H_{15}N_3O_2$ requires C,61.8; H,6.5; N,18.0%.

EXAMPLE 16

1-(3,4-Difluorophenyl)-dihydro-4-methyl-1,2,4-triazine-3,5-(2H,4H)-dione

Methyl [1-(3,4-difluorophenyl)hydrazino]acetate (2.0 g) was treated with methyl isocyanate (0.82 ml) and then with sodium methoxide solution (10 ml) to give the title compound (1.53 g), m.p. 206°–208°.

Analysis Found: C,49.9; H,3.8; N,17.5; $C_{10}H_9F_2N_3O_2$ requires C,49.8; H,3.8; N,17.4%.

EXAMPLE 17

1-(3,5-Difluorophenyl)-dihydro-4-methyl-1,2,4-triazine-3,5-(2H,4H)-dione

Methyl [1-(3,5-difluorophenyl)hydrazino]acetate (1.5 g) was treated with methyl isocyanate (0.61 ml) and then with sodium methoxide solution (7.5 ml) to give a solid (0.98 g). This was purified in a similar manner to the product from Example 15 to give the title compound (0.60 g), m.p. 171°–173°.

Analysis Found: C,49.6; H,4.0; N,17.1; $C_{10}H_9F_2N_3O_2$ requires C,49.8; H,3.8; N,17.4%.

EXAMPLE 18

1-(2,4-Difluorophenyl)-dihydro-4-methyl-1,2,4-triazine-3,5-(2H,4H)-dione

Methyl [1-(2,4-difluorophenyl)hydrazino]acetate (1.0 g) was treated with methyl isocyanate (0.41 ml) and then with sodium methoxide solution (5 ml) to give the title compound (0.73 g), m.p. 167°–169°.

Analysis Found C,49.4; H,3.7; N,17.1; $C_{10}H_9F_2N_3O_2$ requires C,49.8; H,3.8; N,17.4%.

EXAMPLE 19

1-(2,6-Difluorophenyl)-dihydro-4-methyl-1,2,4-triazine-3,5-(2H,4H)-dione

Methyl [1-(2,6-difluorophenyl)hydrazino]acetate (0.8 g) was treated with methyl isocyanate (0.33 ml) and then with sodium methoxide solution (4 ml) to give the title compound (0.43 g), m.p. 152°–155°.

Analysis Found: C,49.4; H,3.7; N,17.0; $C_{10}H_9F_2N_3O_2$ requires C,49.8; H,3.8; N,17.4%.

EXAMPLE 20

Dihydro-1-(3-hydroxyphenyl)-4-methyl-1,2,4-triazine-3,5-(2H,4H)-dione

A solution of dihydro-4-methyl-1-[3-(phenylmethoxy)phenyl]-1,2,4-triazine-3,5-(2H,4H)-dione (0.73 g) in ethanol (150 ml) was hydrogenated at 23° and 1 atmosphere pressure in the presence of 5% palladium on carbon (650 mg) until hydrogen uptake had ceased. The palladium catalyst was removed by filtration and the solvent was removed in vacuo. The resulting oil was triturated with ether to give a solid (0.27 g) which was taken into boiling ethyl acetate and filtered. The filtrate was dried and evaporated to give the title compound (0.22 g), m.p. 95°–96°, t.l.c. (System B, 1:1) Rf 0.32.

EXAMPLE 21

Dihydro-4-methyl-1-(3-propylphenyl)-1,2,4-triazine-3,5-(2H,4H)-dione

Methyl [2-[(methylamino)carbonyl]-1-(3-propylphenyl)hydrazino]acetate (0.5 g) was dissolved in methanol (20 ml) under nitrogen at room temperature. Solid sodium methoxide (0.24 g) was added to the solution which was then stirred at room temperature for 1 h. The reaction mixture was poured into pH 6.5 phosphate buffer solution (10 ml) and extracted with ethyl acetate (3×30 ml). The combined, dried organic phases were concentrated in vacuo and the residual oil was purified by FCC eluting with chloroform:ether (95:5) to give a solid (152 mg) which was triturated with ether to give the title compound (90 mg), m.p. 112°–115°.

Analysis Found: C,62.9; H,7.1; N,16.75; $C_{13}H_{17}N_3O_2$ requires C,63.1; H,6.9; N,17.0%.

EXAMPLE 22

1-(3-Chlorophenyl)-dihydro-4-methyl-1,2,4-triazine-3,5-(2H,4H)-dione

Methyl [1-(3-chlorophenyl)-2-[(methylamino)carbonyl]hydrazino]acetate (700 mg) was dissolved in methanol (25 ml) under nitrogen. Solid sodium methoxide (350 mg) was added to the solution which was then stirred at room temperature for 40 min. The reaction was poured into pH 6.5 phosphate buffer solution (100 ml) and extracted with ethyl acetate (3×70 ml). The combined, dried organic extracts were concentrated in vacuo to give a solid which was triturated with ether (2×20 ml) to give the title compound (352 mg), m.p. 178°–180°.

Analysis Found: C,50.0; H,4.2; N,17.4; $C_{10}H_{10}ClN_3O_2$ requires C,50.1; H,4.2; N,17.5%.

EXAMPLE 23

1-(3-Cyanophenyl)-dihydro-4-methyl-1,2,4-triazine-3,5-(2H,4H)-dione

Methyl [1-(3-cyanophenyl)hydrazino]acetate (700 mg) was dissolved in dry acetonitrile (10 ml) under nitrogen. Methyl isocyanate (0.7 ml) was added to the reaction mixture which was then heated at reflux for 1.5 h. The solvent was removed in vacuo and the oily residue was dissolved in methanol (10 ml) under nitrogen. Sodium methoxide (2.17M solution in methanol; 3.9 ml) was added and the solution was stirred at room temperature for 2 h. The reaction was poured into pH 6.5 phosphate buffer (100 ml) and extracted with ethyl acetate (3×80 ml). The combined, dried organic extracts were concentrated at reduced pressure to give a solid which was triturated with ether (3×20 ml) to give the title compound (640 mg), m.p. 174°–178°. N.m.r. indicated 0.084 mol ethyl acetate.

Analysis Found: C,57.0; H,4.5; N,23.2; $C_{11}H_{10}N_4O_2 \cdot 0.084 \cdot C_4H_8O_2$ requires C,57.3; H,4.5; N,23.6%.

EXAMPLE 24

Dihydro-4-methyl-1-phenyl-1,2,4-triazine-3,5-(2H,4H)-dione

Potassium t-butoxide (11.33 g) was added over 12 min. to a stirred suspension of methyl [2-[(methylamino)carbonyl]-1-phenylhydrazino]-acetate (20.0 g) in methyl isobutyl ketone (200 ml) under nitrogen at 24°–31°. After stirring for 30 min., 1M hydrochloric acid (200 ml) was added at 15°–20°. The resultant suspension was cooled to 0°–5° for 30 min., and the solid was filtered off, washed with water (100 ml) followed by methyl isobutyl ketone (100 ml) and dried in vacuo to give the title compound (13.86 g).

This solid (13.5 g) was further purified by dissolving in THF (270 ml) at reflux and then filtering the solution. The resultant suspension was concentrated to ca. 135 ml, allowed to cool to <25°, and then chilled at 0°–5° for 30 min. The solid was filtered off, washed with THF (27 ml) and dried in vacuo to give the title compound (9.9 g) as microcrystals, m.p. 207°–213° (starts to decompose at 180°).

Analysis Found: C,58.8; H,5.4; N,20.3; $C_{10}H_{11}N_3O_2$ requires C,58.5; H,5.4; N,20.4%.

EXAMPLE 25

Dihydro-4-methyl-1-phenyl-1,2,4-triazine-3,5-(2H,4H)-dione

A mixture of methyl [[2-[(methoxycarbonyl)amino]-1-phenyl]-hydrazino]acetate (1.73 g), methylamine in ethanol (33% w/w; 1.8 ml) and sodium methoxide (8.7 ml of a solution prepared from sodium (4.0 g) and methanol (200 ml)) was stirred at 21° for 2 h. The solution was then heated at 55°–60° under nitrogen for 3 h. T.l.c. (ether) of a sample of the reaction mixture revealed the presence of the title compound, Rf 0.35.

EXAMPLE 26

Dihydro-4-methyl-1-phenyl-1,2,4-triazine-3,5-(2H,4H)-dione

A solution of tetrabutylammonium fluoride (1.0M in THF; 25.3 ml) was evaporated in vacuo and toluene (20 ml) was added to the residue. Azeotropic distillation gave the anhydrous reagent as an oil which was immediately dissolved in freshly distilled THF (15 ml). To this solution was added 2-[(methoxycarbonyl)amino]-N-methyl-1-phenylhydrazineacetamide (1.0 g) and the mixture was heated at reflux over 4A molecular sieves contained in a soxhlet apparatus with THF (15 ml) for 66 h under nitrogen. The title compound was obtained quantitatively as shown by gas chromatography and t.l.c.

The following examples illustrate pharmaceutical formulations according to the invention. The term "active ingredient" is used herein to represent a compound of formula (I).

| 1. Oral Tablet A | |
|---|---|
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in an appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by film coating techniques well known to those skilled in the art. Pigments may be incorporated in the film coat.

| 2. Oral Tablet B | |
|---|---|
| Active Ingredient | 500 mg |
| Lactose | 100 mg |
| Maize Starch | 50 mg |
| Polyvinyl pyrollidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrollidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in the art. Pigments may be incorporated in the film coat.

| 3. Inhalation Cartridge | |
|---|---|
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

We claim:

1. A compound selected from compounds of

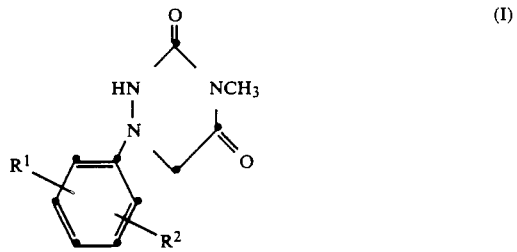

(I)

wherein $R^1$ is selected from the group consisting of hydrogen, halogen, hydroxy, $C_{1-6}$ alkyl, $C_{1-6}$ alkoxy, phenyl $C_{1-3}$ alkoxy (in which the phenyl group is optionally substituted by a substituent selected from halogen, $C_{1-3}$ alkyl, $C_{1-3}$ alkoxy and hydroxy), nitro, trifluoromethyl, cyano, —$CO_2R^3$ (wherein $R^3$ is selected from hydrogen and $C_{1-4}$ alkyl) and —$CONR^4R^5$ (wherein $R^4$ and $R^5$ are each independently selected from hydrogen and $C_{1-4}$ alkyl; and $R^2$ is selected from the group consisting of hydrogen, halogen, hydroxy, $C_{1-6}$ alkyl and $C_{1-6}$ alkoxy; and salts thereof.

2. A compound of claim 1 wherein $R^1$ is selected from the group consisting of halogen, hydroxy, $C_{1-6}$ alkyl, $C_{1-6}$ alkoxy, phenyl $C_{1-3}$ alkoxy (in which the phenyl group is optionally substituted by a substituent selected from halogen, $C_{1-3}$ alkyl, $C_{1-3}$ alkoxy and hydroxy), nitro, trifluoromethyl, cyano, —$CO_2R^3$ and —$CONR^4R^5$; and physiologically acceptable salts thereof.

3. A compound of claim 1 wherein $R^1$ is selected from the group consisting of hydrogen, halogen, hydroxy, $C_{1-6}$ alkyl, $C_{1-6}$ alkoxy, phenyl $C_{1-3}$ alkoxy, trifluoromethyl and cyano, and $R^2$ is selected from the group consisting of hydrogen, halogen, and $C_{1-6}$ alkyl; and physiologically acceptable salts thereof.

4. A compound of claim 3 wherein $R^1$ is selected from the group consisting of hydrogen, halogen and phenyl $C_{1-3}$ alkoxy, and $R^2$ is hydrogen; and physiologically acceptable salts thereof.

5. A compound of claim 4 wherein R[1] is fluorine, and R[2] is hydrogen, and physiologically acceptable salts thereof.

6. The compound of claim 1 which is dihydro-1-(3-fluorophenyl)-4-methyl-1,2,4-triazine-3,5-(2H,4H)-dione; and physiologically acceptable salts thereof.

7. A compound of claim 1 selected from dihydro-1-(4-fluorophenyl)-4-methyl-1,2,4-triazine-3,5-(2H,4H)-dione; and dihydro-4-methyl-1-phenyl-1,2,4-triazine-3,5-(2H,4H)-dione; and physiologically acceptable salts thereof.

8. A pharmaceutical composition comprising, as active ingredient, at least one compound of claim 1 or a physiologically acceptable salt thereof in association with a pharmaceutical carrier or excipient.

9. A method of treatment of a human or animal subject suffering from or susceptible to diseases in which leukotrienes or other 5-lipoxygenase products are mediators, which comprises administering to the subject an effective amount of a compound selected from compounds of formula

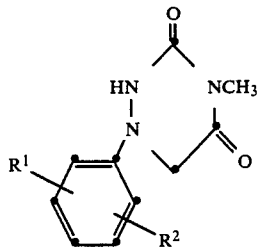

wherein R[1] is selected from the group consisting of hydrogen, halogen, hydroxy, $C_{1-6}$ alkyl, $C_{1-6}$ alkoxy, phenyl $C_{1-3}$ alkoxy (in which the phenyl group is optionally substituted by a substituent selected from halogen, $C_{1-3}$ alkyl, $C_{1-3}$ alkoxy and hydroxy), nitro, trifluoromethyl, cyano, —$CO_2R^3$ (wherein R[3] is selected from hydrogen and $C_{1-4}$ alkyl) and —$CONR^4R^5$ (wherein R[4] and R[5] are each independently selected from hydrogen and $C_{1-4}$ alkyl; and R[2] is selected from the group consisting of hydrogen, halogen, hydroxy, $C_{1-6}$ alkyl and $C_{1-6}$ alkoxy; or a physiologically acceptable salt thereof.

10. The method of claim 9 wherein the compound is dihydro-1-(3-fluorophenyl)-4-methyl-1,2,4-triazine-3,5-(2H,4H)-dione or a physiologically acceptable salt thereof.

11. The method of claim 9 wherein the compound is selected from dihydro-1-(4-fluorophenyl)-4-methyl-1,2,4-triazine-3,5-(2H,4H)-dione; dihydro-4-methyl-1-phenyl-1,2,4-triazine-3,5-(2H,4H)-dione; or a physiologically acceptable salt thereof.

* * * * *